US005762951A

United States Patent [19]

Maasz et al.

[11] Patent Number: 5,762,951
[45] Date of Patent: Jun. 9, 1998

[54] EFFERVESCENT COMPOSITION AND TABLET MADE THERE FROM

[75] Inventors: Joachim Maasz, Leichlingen; Christian Fritsch, Erlangen; Werner Gräwingholt, Cologne; Bernhard Streuff, Wermelskirchen; Georg Frank, Wuppertal, all of Germany

[73] Assignee: Bayer Aktiengesellschaft, Leverkusen, Germany

[21] Appl. No.: 97,935

[22] Filed: Jul. 26, 1993

Related U.S. Application Data

[63] Continuation of Ser. No. 750,354, Aug. 27, 1991, abandoned.

[30] Foreign Application Priority Data

Sep. 4, 1990 [DE] Germany .................. 40 27 927.8

[51] Int. Cl.$^6$ .................. A61K 9/46; A61K 9/20
[52] U.S. Cl. .................. 424/439; 252/183.13; 514/159; 514/165; 424/466; 562/584; 562/585
[58] Field of Search .................. 252/182.12, 183.13; 562/584, 585; 424/466, 439; 514/159, 165

[56] References Cited

U.S. PATENT DOCUMENTS

| | | | |
|---|---|---|---|
| 3,518,343 | 6/1970 | Welsh et al. | 424/44 |
| 3,663,271 | 5/1972 | Gerfely | 428/403 |
| 3,773,922 | 11/1973 | Gergely | |
| 3,882,228 | 5/1975 | Boncey et al. | 424/489 |
| 4,632,843 | 12/1986 | Pich et al. | 424/452 |
| 4,650,669 | 3/1987 | Alexander et al. | 424/44 |
| 4,767,729 | 8/1988 | Osman et al. | 501/94 |
| 4,824,664 | 4/1989 | Tarral et al. | |
| 4,888,177 | 12/1989 | Gergely et al. | 424/466 |
| 4,911,930 | 3/1990 | Gergely et al. | 424/466 |
| 5,037,657 | 8/1991 | Jones et al. | 424/466 |
| 5,045,459 | 9/1991 | Mothes et al. | 435/144 |
| 5,064,656 | 11/1991 | Gergely et al. | 424/463 |
| 5,071,874 | 12/1991 | Scholl et al. | 514/561 |
| 5,102,665 | 4/1992 | Schaeffer | 424/466 |
| 5,104,799 | 4/1992 | Mothes et al. | 435/144 |
| 5,108,761 | 4/1992 | Andon et al. | 426/2 |
| 5,149,552 | 9/1992 | Vidal et al. | 426/321 |
| 5,186,965 | 2/1993 | Fox et al. | 426/74 |
| 5,194,270 | 3/1993 | Cante et al. | 426/74 |
| 5,415,870 | 5/1995 | Gergely et al. | 424/466 |
| 5,503,846 | 4/1996 | Wehling et al. | 424/466 |

FOREIGN PATENT DOCUMENTS

| | | |
|---|---|---|
| 0219337 | 10/1986 | European Pat. Off. |
| 1274797 | 5/1972 | United Kingdom |

OTHER PUBLICATIONS

International Journal of Pharmaceutics, 45, (1988) 19–26, S.I. Saleh, et al.

*Primary Examiner*—Edward A. Miller
*Attorney, Agent, or Firm*—Sprung Horn Kramer & Woods

[57] ABSTRACT

The present invention relates to an acidic effervescent component for direct tableting of effervescent tablets and a process for its preparation.

10 Claims, No Drawings

EFFERVESCENT COMPOSITION AND TABLET MADE THERE FROM

This application is a continuation of application Ser. No. 750,354 filed Aug. 27, 1991, now abandoned.

The present invention relates to an acidic effervescent component for direct tableting of effervescent tablets and a process for its preparation.

Effervescent tablets customarily consist of the active compound, an effervescent composition and, if desired, other auxiliaries. The effervescent composition consists of an acidic component such as, for example, citric or tartaric acid or another physiologically acceptable acid and an alkaline component such as, for example, sodium carbonate, potassium carbonate or calcium carbonate, or sodium bicarbonate and potassium bicarbonate, in whose reaction with one another gaseous carbon dioxide is formed. As an alternative to the acids mentioned, their acidic salts or mixtures of the acids with the salts can also be used (cf. DOS (German Offenlegungsschrift) 1,962,791).

As both the acidic and the basic component of the effervescent composition can only be directly tableted with great difficulty, prior granulation of a part of these components or of all components of the effervescent tablet is as a rule necessary (cf. DE 2,553,444, DE 2,216,072 or EP 233,853). However, the prior granulation of individual components or of all components of an effervescent tablet is associated with high outlay in terms of apparatus, finance and time. Often, in addition to the pregranulation, binders additionally still have to be employed. In the past, therefore, direct tableting of the starting components was repeatedly attempted, for example by use of special binders (cf. EP 219,337). These special binders such as, for example, dextrose are an unnecessary component for the efficacy of the effervescent tablet. In addition to increasing the size of the tablet, it has the disadvantage of having a caloric nutritive value and as a carbohydrate is unsuitable for diabetics, as it cannot be ignored in the amounts of 200–400 mg/tablet required.

It was also attempted to achieve direct tableting by spray drying of sodium bicarbonate as the basic component (cf. Saleh et al., Int. J. Pharm. 45 (1988) 19–26). However, this was only carried out with the addition of other auxiliaries, such as, for example, of binder. Other disadvantages of the process described therein which can be mentioned are the uneconomical and complicated carrying-out of the process. Owing to the low solubility of sodium bicarbonate in water, only an approximately 7% strength solution of sodium bicarbonate can be spray dried. The spray drying of more highly concentrated suspensions is of little use for sodium bicarbonate owing to its thermal decomposition at temperatures above 50° C.

It has been found that the new acidic effervescent components which were prepared by spray drying no longer have these disadvantageous tableting properties. Using them, direct tableting of effervescent tablets in a simple manner and without additional binders is possible.

The invention relates to a new acidic spray-dried effervescent component, which is essentially spherical and contains an acidic salt of tartaric and/or citric acid. Of particular interest are effervescent components according to the invention which essentially contain mono- or disodium citrate, mono- or dipotassium citrate, mono- or diammonium citrate, monosodium, monopotassium or monoammonium tartrate or mixtures of these salts. Monosodium citrate may be particularly preferably mentioned.

Acidic effervescent components in the form of spherical individual particles having an average particle size of 70 to 250 μm and a bulk volume of 110 to 350 ml/100 g are particularly suitable.

An average particle size of 100 to 190 μm and a bulk volume of 130 to 270 ml/100 g are particularly preferred.

The invention also relates to a process for the preparation of the directly tabletable acidic effervescent component, characterised in that acidic salts of tartaric or citric acid are spray-dried. In this connection, customary spray drying processes, for example continuous or batchwise spray drying in the continuous current, counter current or mixed current process, spray agglomeration, spray drying in or onto a pulverulent fluidised bed and similar processes are used.

In a preferred embodiment, a solution or suspension of the said acidic salts in a suitable solvent or solvent mixture is initially prepared as a feed liquid in the spray drying process according to the invention in such a way that the solids content is 10 to 70%, preferably 30 to 50%, of the finished feed liquid, and this feed liquid is then dried in a customary spray dryer at an air inlet temperature of 100° to 250° C., preferably 120° to 210° C., and an air outlet temperature of 40° to 170° C., preferably 50° to 140° C.

The acidic effervescent component having essentially spherical particles which is prepared in this way can be directly tableted in an advantageous manner to give stable effervescent tablets without additional binders being necessary. The acidic effervescent component according to the invention, whose individual particles are essentially obtained in spherical form, which, depending on the drying parameters, can contain cavities of different size, is superior in its tableting properties to the known granules of acidic effervescent components. In particular, the hardness and abrasion resistance of effervescent tablets which have been prepared using the effervescent component according to the invention are essentially better than that of comparable effervescent tablets which have been prepared by pregranulation of the acidic effervescent component. Surprisingly, the dissolution time of the effervescent tablet is not increased by the improved hardness and abrasion resistance of the tablets but even slightly reduced by the preparations according to the invention.

The present invention is suitable to meet the long-existing need for simple production of stable effervescent tablets having advantageous properties. The following advantages may be mentioned in particular:

a) The spherical acidic effervescent component can be prepared in a simple manner, if desired continuously, and without the use of undesired auxiliaries.

b) Effervescent tablets can be tableted directly, i.e. without prior granulation of individual constitents, by the use of this acidic component.

c) Owing to the high stability of the acidic effervescent component, tableting can be carried out at higher pressures and at a higher speed, for example even in high-capacity presses.

d) No additional binders, solubilisers or disintegration promoters are necessary in the production of the effervescent tablets.

e) The hardness and abrasion resistance of the effervescent tablets produced according to the invention is improved, which leads to a higher mechanical stability of the tablets and simplifies packing and transport.

f) Despite greater hardness, the dissolution time of the effervescent tablets produced according to the invention is reduced.

The acidic effervescent component according to the invention can be employed in many ways, for example in the field of pharmacy and cosmetics, but also in foodstuffs and products in the veterinary field. It can be employed in all forms in which effervescent preparations are used, for example in the form of tablets, granules or powders. Pharmaceutical use is particularly preferred. In this connection, the effervescent component according to the invention can be combined with all types of active compounds which can be administered in an effervescent preparation. Of particular interest are analgesics such as, for example, acetylsalicylic acid, paracetamol, ibuprofen, ketoprofen and naproxen, in each case in racemic form or in the form of their pure enantiomers, or antacids, vitamins, psychotherapeutics and other orally administrable active compounds, in particular active compounds for the treatment of coughs, stomach disorders and colds.

The exemplary embodiments below are intended to illustrate the subject of the invention in more detail without restricting it.

EXAMPLES

Example 1

40.8 kg of monosodium citrate are suspended in 59.2 kg of demineralised water and the suspension is then spray-dried at an air inlet temperature of 210° C. and an air outlet temperature of 140° C. The spray-dried sodium citrate has an average particle size of 125 μm and a bulk volume of 260 ml/100 g.

Example 2

40.8 kg of monosodium citrate are dissolved in 59.2 kg of demineralised water with warming and the solution is dried at an air inlet temperature of 150° C. and an air outlet temperature of 100° C. The spray-dried sodium citrate has an average particle size of 120 μm and a bulk volume of 162 ml/100 g.

Example 3

37.3 kg of citric acid are dissolved in 32.1 kg of demineralised water and the solution is reacted to give monosodium citrate by addition of 17.3 kg of 45% strength sodium hydroxide solution. A solids content of 41.6% of monosodium citrate results. After spray drying at an air inlet temperature of 120° C. and an air outlet temperature of 60° C., spray-dried sodium citrate having an average particle size of 100 μm and a bulk volume of 158 ml/100 g is obtained.

Example 4

37.3 kg of citric acid are dissolved in 45.1 kg of demineralised water, and the solution is reacted to give monopotassium citrate by addition of 24.4 kg of 45% strength potassium hydroxide solution and spray-dried analogously to Example 3.

Example 5

45 kg of monosodium tartrate are suspended in 55 kg of demineralised water and the suspension is spray-dried at an air inlet temperature of 130° C. and an air outlet temperature of 70° C. The spray-dried monosodium tartrate has an average particle size of 110 μm and a bulk volume of 145 ml/100 g.

Example 6

45 kg of the effervescent components according to the invention, prepared according to Examples 1 and 3, are in each case mixed with 12.5 kg of acetylsalicylic acid, 28.5 kg of sodium bicarbonate and 6 kg of sodium carbonate and the mixture is compressed in a tablet press to give tablets having a weight of 3.2 g. For comparison, 45 kg of sodium citrate granules containing 20% by weight of citric acid as a binder are used instead of the effervescent component according to the invention. The resultant tablet hardnesses and disintegration times show a distinct improvement when using the effervescent component according to the invention (see table).

| Acidic effervescent component used | Average tablet hardness | Average disintegration time |
|---|---|---|
| Monosodium citrate prepared according to Example 1 | 120 N | 50 s |
| Monosodium citrate prepared according to Example 3 | 128 N | 55 s |
| Monosodium citrate granules containing 20% of citric acid | 72 N | 90 s |

Example 7

51.2 kg of monosodium citrate are suspended in 68.8 kg of demineralised water and the suspension is dried in a spray agglomeration unit at an air inlet temperature of 125° C. and an air outlet temperature of 55° C. The product temperature in the fluidised bed is 58° C. The product has a mean particle size of 100 μm and a bulk volume of 202 ml/100 g. 45 kg of this spray-agglomerated monosodium citrate are mixed with 12.5 kg of acetylsalicylic acid, 28.5 kg of sodium bicarbonate, 7 kg of ascorbic acid and 6 kg of sodium carbonate, and the mixture is compressed in a tablet press to give tablets having a weight of 3.2 g. The tablets have a hardness of about 118N and a disintegration time of about 1 minute.

Example 8

8.4 kg of ranitidine hydrochloride are mixed with 48 kg of spray-dried monosodium tartrate, 57.5 kg of sodium bicarbonate, 2.5 kg of sodium cyclamate, 10 kg of micronised fumaric acid and 8.5 kg of lemon-lime flavouring, and the mixture is conditioned to a relative equilibrium humidity of at most 10% and compressed to give tablets having a diameter of 22 mm and a weight of 2.5 g.

Example 9

10 kg of ibuprofen are mixed with 75 kg of spray-dried monopotassium citrate, 35 kg of sodium bicarbonate, 22.5 kg of sodium carbonate and 2.5 kg of polyvinylpyrrolidone, and the mixture is compressed to give tablets having a diameter of 24 mm and a weight of 3 g.

Example 10

10 kg of acetylcysteine are mixed with 42.5 kg of spray-dried monosodium citrate, 15 kg of sodium bicarbonate, 5 kg of micronised adipic acid, 1.5 kg of polyethylene glycol 6000, 0.5 kg of sodium stearyl fumarate and 0.5 kg of a suitable flavouring, and the mixture is compressed to give tablets having a diameter of 18 mm and a weight of 1.5 g.

Example 11

3 kg of ambroxol hydrochloride are mixed with 80 kg of spray-dried monosodium citrate, 30 kg of sodium bicarbonate, 10 kg of micronised adipic acid, 5 kg of polyethylene glycol 6000, 1 kg of sodium stearyl fumarate and 1 kg of suitable flavouring, and the mixture is compressed to give tablets having a diameter of 17 mm and a weight of 1.3 g.

We claim:

1. A directly tabletable effervescent composition consisting essentially of an acidic component which is a spray-dried acidic salt in the form of substantially spherical particles and an alkaline component which is effective upon reaction to form gaseous $CO_2$ wherein the acidic salt is at least one of mono- or disodium citrate, mono- or dipotassium citrate, mono- or diammonium citrate, monosodium, monopotassium or moroammonium tartrate having an average particle size of 100 to 190 µm and a bulk volume of 130 to 150 ml/100 g.

2. The directly tabletable effervescent composition according to claim 1, which is further admixed with an active ingredient.

3. A tablet which has been directly tableted from ingredients consisting essentially of the composition according to claim 2.

4. A tablet according to claim 3, weighing about 3.2 grams, the tablet by weight approximately consisting essentially of 40.8 parts of monosodium citrate of average particle size of about 125 µm and a bulk volume of about 158 ml/100 g, 12.5 parts of acetylsalicylic acid, 28.5 parts of sodium bicarbonate, and 6 parts of sodium carbonate.

5. A tablet according to claim 3, weighing about 3.2 grams, the tablet by weight approximately consisting essentially of 40.8 parts of monosodium citrate of average particle size of about 100 µm and a bulk volume of about 202 ml/100 g, 12.5 parts of acetylsalicylic acid, 28.5 parts of sodium bicarbonate, and 6 parts of sodium carbonate.

6. A tablet according to claim 3 weighing about 2.3 grams, by weight approximately consisting essentially of 8.4 parts of ranitidine hydrochloride, 48 carts of monosodium tartrate, 57.5 parts of sodium bicarbonate, 2.5 parts of sodium cyclamate, 10 parts of fumaric acid, and 8.5 parts of lemon-lime flavoring.

7. A tablet according to claim 3 weighing about 3 grams, by weight approximately consisting essentially of 10 parts of ibuprofen, 75 parts of monopotassium citrate, 35 parts of sodium bicarbonate, 22.5 parts of sodium carbonate, and 2.5 parts of polyvinyl pyrrolidone.

8. A tablet according to claim 3 weighing about 1.5 grams, by weight approximately consisting essentially of 10 parts of acetyl cysteine, 42.5 parts monosodium citrate, 15 parts of sodium bicarbonate, 5 parts of adipic acid, 1.5 parts of polyethylene glycol 6000, 0.5 part of stearyl fumarate, and 0.5 part of a flavoring agent.

9. A tablet according to claim 3 weighing about 1.3 grams, by weight approximately consisting essentially of 3 parts of ambroxol hydrochloride, 80 parts of monosodium citrate, 30 parts of sodium bicarbonate, 10 parts of adipic acid, 5 parts of polyethylene glycol 8000, 1 part sodium stearyl fumarate, and 1 part a flavoring agent.

10. A tablet according to claim 3 weighing about 3.2 grams, particles by weight approximately consisting essentially parts of acidic spherical particles of monosodium citrate of 45 parts of acidic spherical particles of monosodium citrate of an average particle size of about 125 µm and a bulk volume of about 260 ml./100 g, 12.5 parts of acetylsalicylic acid, 28.5 parts of sodium bicarbonate, and 6 parts of sodium carbonate.

* * * * *

UNITED STATES PATENT AND TRADEMARK OFFICE
CERTIFICATE OF CORRECTION

PATENT NO.    : 5,762,951
DATED         : June 9, 1998
INVENTOR(S)   : Joachim Maasz et al It is certified that error appears in the above-identified patent and that said Letters Patent is hereby corrected as shown below:

| | |
|---|---|
| Column 5, Line 14 | Delete "moroammonium" and substitute --monoammonium-- |
| Column 5, Line 45 | Delete "ranitidine" and substitute --renitidine-- |
| Column 5, Line 46 | Delete "carts" and substitute --parts-- |
| Column 6, Line 37-38 | After "essentially" delete "parts of acidic spherical particles of monosodium citrate" |

Signed and Sealed this

Fourteenth Day of December, 1999

Attest:

Attesting Officer

Q. TODD DICKINSON

Acting Commissioner of Patents and Trademarks